US00RE37314E

(19) United States
(12) Reissued Patent
Hirai et al.

(10) Patent Number: US RE37,314 E
(45) Date of Reissued Patent: Aug. 7, 2001

(54) PYRIMIDINE DERIVATIVES

(75) Inventors: Kentaro Hirai, Kyoto; Teruyuki Ishiba, Osaka; Haruo Koike, Kyoto; Masamichi Watanabe, Shiga, all of (JP)

(73) Assignee: Shionogi Seiyaku Kabushiki Kaisha, Osaka (JP)

(21) Appl. No.: 09/141,731

(22) Filed: Aug. 27, 1998

Related U.S. Patent Documents

Reissue of:
(64) Patent No.: 5,260,440
Issued: Nov. 9, 1993
Appl. No.: 07/897,793
Filed: Jun. 12, 1992

(30) Foreign Application Priority Data

Jul. 1, 1991 (JP) ..... 3-188015

(51) Int. Cl.[7] ..... A61K 31/505; C07D 239/34; C07D 239/38; C07D 239/42
(52) U.S. Cl. ..... 514/316; 544/318; 544/322
(58) Field of Search ..... 514/756; 544/297

(56) References Cited

U.S. PATENT DOCUMENTS 4,868,185 9/1989 Chucholowski et al. ..... 514/256
4,925,852 5/1990 Kesseler et al. ..... 514/256
5,026,708 6/1991 Fujikawa et al. ..... 514/256

FOREIGN PATENT DOCUMENTS 0 330 057 8/1989 (EP) .
0 367 895 5/1990 (EP) .

OTHER PUBLICATIONS

Moore et al, J. Am. Chem. Soc., vol. 107, pp. 3694–3701, 1985.*

G. Beck et al., *J. Med. Chem.,* 33, 52–60 (1990).

B. Roth et al., *J. Med. Chem.,* 34, 463–466 (1991).

* cited by examiner

*Primary Examiner*—Richard L. Raymond
(74) *Attorney, Agent, or Firm*—Pillsbury Madison & Sutro, LLP Intellectual Property Group

(57) ABSTRACT

The compounds of the present invention inhibit the HMG-CoA reductase, and subsequently suppress the biosynthesis of cholesterol. And they are useful in the treatment of hypercholesterolemia, hyperlipoproteinemia, and atherosclerosis.

3 Claims, No Drawings

PYRIMIDINE DERIVATIVES

Matter enclosed in heavy brackets [ ] appears in the original patent but forms no part of this reissue specification; matter printed in italics indicates the additions made by reissue.

*This application is a reissue of U.S. Pat. No. 5,260,440, issued Nov. 8, 1993.*

BACKGROUND OF THE INVENTION

1. Field of the Invention

The present invention relates to 3-hydroxy-3-methylglutaryl coenzyme A (HMG-CoA) reductase inhibitor.

2. Prior Art

As the first generation of drugs for the treatment of atherosclerosis by inhibiting the activity of HMG-CoA reductase, there are known Mevinolin (U.S. Pat. No. 4,231,938), pravastatin sodium (U.S. Pat No. 4,346,227), and, simvastatin (U.S. Pat. No. 4,444,784), which are fungal metabolites or of the chemical modifications. Recently, synthetic inhibitors of HMG-CoA reductase such as fluvastatin (F. G. Kathawala et al., 8th Int'l Symp. on Atherosclerosis, Abstract Papers, p. 445, Rome (1988)) and BMY 22089 (GB Pat. No. 2,202,846) are developed as the second generation drugs.

SUMMARY OF THE INVENTION

The compounds of the present invention inhibit the HMG-CoA reductase, which plays a main role in the synthesis of cholesterol, and subsequently they suppress the biosynthesis of cholesterol. Therefore, they are useful in the treatment of hypercholesterolemia, hyperlipoproteinemia, and atherosclerosis.

DETAILED DESCRIPTION

The present invention relates to compounds of the formula (I):

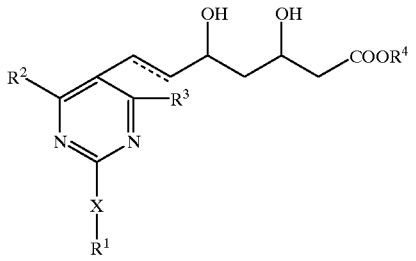

wherein $R^1$ is lower alkyl, aryl or aralkyl, each of which may have one or more substituents: $R^2$ and $R^3$ each is independently hydrogen, lower alkyl, or aryl, and each of said lower alkyl and aryl may have one or more substituents; $R^4$ is hydrogen, lower alkyl, or a cation capable of forming a non-toxic pharmaceutically acceptable salt; X is sulfur, oxygen, or sulfonyl, or imino which may have a stubstituent; the dotted line represents the presence or absence of a double bond, or the corresponding ring-closed lactone. This invention also provides a pharmaceutical composition comprising the same.

In the specification, the term "lower alkyl" refers to a straight, branched, or cyclic $C_1$ to $C_6$ alkyl, including methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, and isohexyl and the like. Further, the lower alkyl may be substituted by 1 to 3 substituents independently selected from the group consisting of halogen, amino, and cyano. Halogen means fluorine, chlorine, bromine and iodine.

The term "aryl" refers to $C_6$ to $C_{12}$ aromatic group including phenyl, tolyl, xylyl, biphenyl, naphthyl, and the like. The aryl may have 1 to 3 substituents independently selected from the group consisting of lower alkyl, halogen, amino, and cyano. Preferred aryl is phenyl substituted by 1 to 3 halogens.

The term "aralkyl" refers to $C_1$ to $C_6$ lower alkyl substituted by $C_6$ to $C_{12}$ aromatic aryl group defined above. Examples of them are benzyl, phenethyl, phenylpropyl and the like, each of which may have 1 to 3 substituents independently selected from the group consisting of lower alkyl halogen, amino, cyano, and the like.

The term "a cation capable of forming a non-toxic pharmaceutically acceptable salt" refers to alkali metal ion, alkaline earth metal ion, and ammonium ion. Examples of alkali metal are lithium, sodium, potassium, and cesium, and examples of alkaline earth metal are beryllium, magnesium, and calcium. Especially, sodium and calcium are preferred.

Examples of "acyl" are formyl acetyl, propionyl, butyryl, isobutyryl, valeryl, and isovaleryl.

In the term "imino which may have a substituent", preferred substituents are acyl, optionally substituted amino, and substituted sulfonyl.

The term "substituted amino as substituent" means amino group substituted by sulfonyl and alkylsulfonyl. Examples of them are sulfonyl amino and methanesulfonyl amino.

The term "substituted sulfonyl as substituent" means sulfonyl group substituted by alkyl, amino, or alkylamino. Examples of them are methanesulfonyl, sulfamoyl, methylsulfamoyl, and N-methylsulfamoyl.

The compounds of the present invention can be prepared by the following method.

(1) The carboxylate group of the compound a is converted into the alcohol group by the reduction in an appropriate inactive solvent such as THF, ether, and toluene in the presence of the reductant such as LiAlH and DIBAL-H. The reaction is performed at −70° to 50° C., preferably at near room temperature, for 10 minutes to 10 hours, preferably for 30 minutes to 3 hours. Then the obtained alcohol is subjected to oxidation in an appropriate solvent such as methylene chloride in the presence of the oxidizing agent such as TPAP/4-methylmorpholin-N-oxide or pyridium chlorochromate to give aldehyde compound b. The reaction is performed at 0°–60° C., preferably at near room temperature, for 10 minutes to 10 hours, preferably 30 minutes to 3 hours.

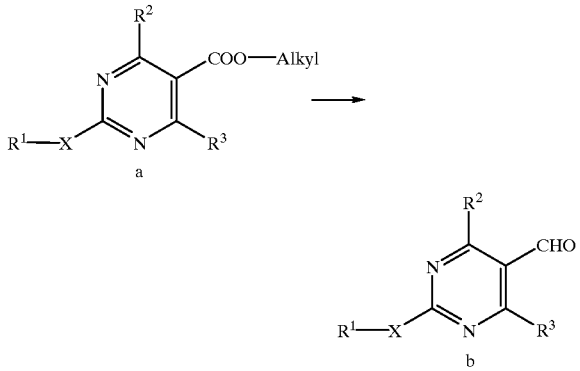

wherein $R^1$, $R^2$, and $R^3$ each has the same meaning as defined above, and Alkyl means lower alkyl.

(2) The obtained compound b is subjected to reaction with (3R)-or (3S)-3-(tert-butyldimethylsilyloxy-5-oxo-6-triphenylphosphoranylidene hexanoic acid derivatives in an appropriate solvent such as acetonitrile, diethylether, tetrahydrofuran, and dimethylformamide to give the compound c. The reaction is performed for 1–30 hours, preferably for 10–15 hours under heating.

c

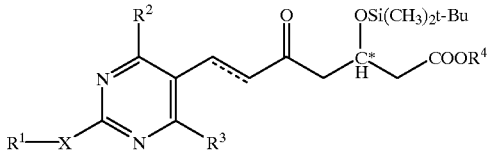

wherein C* means asymmetric carbon atom, the dotted line means the presence or absence of the double bond, $R^1$, $R^2$, $R^3$, and $R^4$each has the same meaning as defined above.

(3) The compound c is subjected to elimination of the tertbutyldimethylsilyl group in an appropriate organic solvent in the presence of hydrogen halogenide to give the compound d.

Every sort of halogen can be used for hydrogen halogenide. Amongst all, hydrogen fluoride is preferred.

The same organic solvents as used in the step (2) may be employed. Acetonitrile is especially preferred.

The reaction is performed in a range of from 0° to 60° C., preferably at room temperature, for 0.5–10 hours, preferably for 1–2 hours.

d

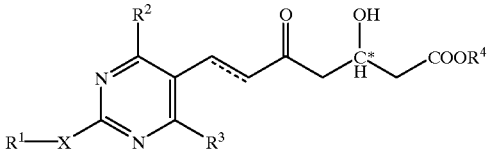

wherein C*, the dotted line, $R^1$, $R^2$, $R^3$, and $R^4$ each has the same meaning as defined above.

(4) The compound d is reacted with diethylmethoxyborane and $NaBH_4$ in an alcohol-organic solvent mixture and subjected to column chromatography of silica gel to give the compound (I) (in case $R^4$ is lower alkyl). The reaction is performed at a temperature between −100° to 20° C., preferably between −85° to −70° C. under cooling, for 10 minutes to 5 hours, preferably for 30 minutes to 2 hours.

Here, the alcohol includes methanol, ethanol, propanol, and butanol; and the organic solvent includes the same as in the step (3).

Further, if necessary, the obtained compound may be subjected to saponification with the solution of metalic hydroxide ($R^4$: cation), and after the saponification, the reaction mixture is neutralized with an acid and extracted with an organic solvent ($R^4$: hydrogen). The saponification is performed in a popular solvent such as water, acetonitrile, dioxane, acetone, and the mixture thereof, preferably in the presence of a base, by a conventional method. The reaction is performed at 0° to 50° C., preferably at near room temperature.

As metalic hydroxide which may be used are sodium hydroxide, potassium hydroxide, and their analogue.

Acids which may be used include inorganic acids such as hydrochloric acid, sulfuric acid and the like.

(I)

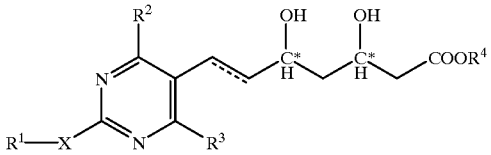

wherein C*, the dotted line, $R^1$, $R^2$, $R^3$, and $R^4$ each has the same meaning as defined above.

Further, if necessary, the obtained compounds (I) are subjected to reflux under heating to give the corresponding lactones.

The compound of the present invention can be administered orally or parenterally. For example, the compound of the present invention may be orally administered in the form of tablets, powders, capsules and granules, aqueous or oily suspension, or liquid form such as syrup or elixir, and parenterally in the form of aqueous or oily suspension.

These preparations can be prepared in a conventional manner by using excipients, binders, lubricants, aqueous or oily solubilizers, emulsifier, suspending agents, and the like. And preservatives and stabilizers can be further used.

The dosages may vary with the administration route, age, weight, condition, and the kind of disease of the patients, but are usually 0.5–200 mg/day, preferably 1–100 mg/day through oral route, and 0.1–100 mg/day, preferably 0.5–50 mg/day through parenteral route. They may be used in a single or divided doses.

The present invention is illustrated by the following examples and reference examples, which are not to be considered as limiting.

The abbreviations used in examples and reference examples have the following meanings.

Me: methyl,
Et: ethyl,
i-Pr: isopropyl
t-Bu: tert-butyl,
Ph: phenyl,
DMF: dimethylformamide,
THF: tetrahydrofuran
DDQ: 2,3-dichloro-5,6-dicyano-1,4-benzoquinone
TPAP: tetrapropylammonium perruthenate
HMPA: hexamethylphosphoramide
DIBAL-H: diisobutylaluminum hydride.

REFERENCE EXAMPLE 1

Ethyl 4-(4-fluorophenyl)-6-isopropyl-2-methylthiopyrimidine-5-carboxylate (III-1) and Ethyl 4-(4-fluorophenyl)-6-isopropyl-2-methylsulfonylpyrimidine-5-carboxylate (III-2)

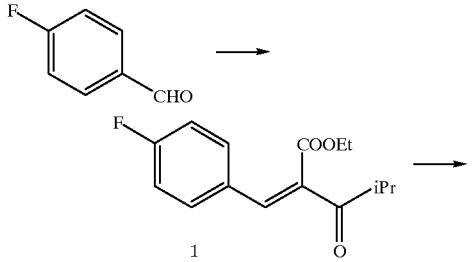

-continued

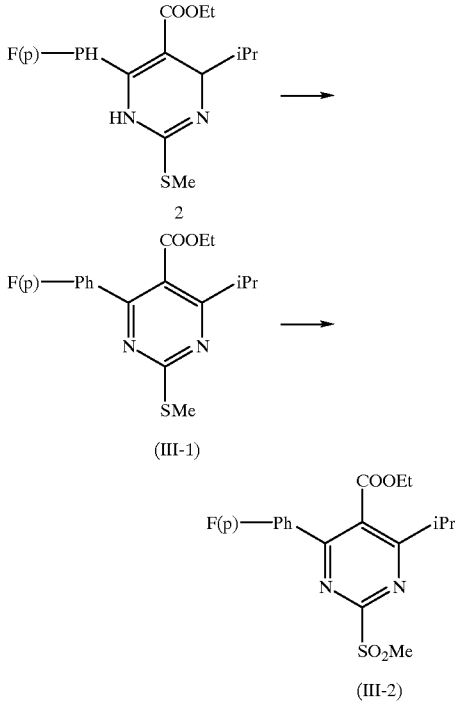

p-Fluorobenzaldehyde 81.81 g is reacted in the same manner as disclosed in the specification of JP Unexamed. Pat. Publn. No. 61-40272 to give 151.0 g (Yield: 86.7%) of the compound 1. Then the mixture of a solution of 44.68 g of the compound 1 in 65 ml of HMPA and 28.24 g of s-methylisourea hydrogen sulfate is stirred at 100° C. for 22 hours. Then the reaction mixture is extracted with ether, and washed with saturated sodium hydrogencarbonate and water in order. The organic layer is dried, and the solvent is distilled away. The obtained residue is subjected to column chromatography of silica gel to give 26.61 g (yield: 46.8%) of the compound 2.

To a solution of the obtained compound 2 in 400 ml of benzene is added 21.64 g (0.095 mmol) or DDQ, and the mixture is stirred for 30 minutes. Then the mixture is subjected to column chromatography of silica gel to give 24.31 g (Yield: 91.9%) of the compound (III-1).

NMR ($CDCl_3$) δ: 1.10 (t, J=7,3H): 1.31 (d, J=7,6 Hz); 2.61 (s, 3H); 3.18 (hept, J=7,1H); 4.18 (q, J=7,2H); 7.12 (m, 2H), 7.65 (m, 2H).

To a solution of 13.28 g (0.04 mmol) of the compound (III-1) in chloroform is added 17.98 g of m-chloroperbenzoic acid, and the reaction mixture is stirred at room temperature. Then it is washed with sodium sulfate and saturated sodium hydrogencarbonate in order. The solution is dried, and the solvent is distilled away and washed with n-hexane to give 13.93 g (Yield 95.7%) of the compound (III-2).

NMR ($CDCl_3$) δ: 1.16 (t, J=7,3H); 1.37 (d, J=7,6H); 3.26 (hept, J=7,1H); 3.42 (s, 3H), 4.28 (q, 2H); 7.18 (m, 2H); 7.76 (m, 2H).

REFERENCE EXAMPLE 2

Another synthetic method of the compound (III-1)

To a solution of 200 mg (0.594 mmol) of the compound 2 in 5 ml of dichloromethane are added 0.5 g (6.10 equivalent) of potassium carbonic anhydride and 166 mg (1.1 equivalent) of iodine, and the mixture is stirred at room temperature for 2.5 hours. After reaction, to the mixture is added saturated sodium hydrogensulfite and extracted with ether. The organic layer is washed with water and dried. The solvent is distilled away under reduced pressure to give 166 mg (Yield: 83.6%) of the compound (III-1) as resinous substance.

NMR ($CDCl_3$) δ: 1.10 (t, 3H, J=7); 1.31 (d, 6H, J=7); 2.61 (s, 3H) 3.17 (heptet, 1H, J=7); 4.18 (q, 2H, J=7); 7.07–7.17 (m, 2H); 7.61–7.69 (m, 2H)

REFERENCE EXAMPLE 3

Another synthetic method of the compound (III-2)

To a solution of 1.0 g (2.97 mmol) of the compound 2 in 10 ml of acetone is added 1.5 g (9.48 mmol) of potassium permanganate, and the mixture is stirred at room temperature for 15 minutes. Acetic acid 1.0 ml is added thereto, and the mixture is stirred at room temperature for further 30 minutes and water is added thereto. The reaction mixture is extracted with ether, washed with saturated sodium hydrogencarbonate and saturated brine and dried over anhydrous magnesium sulfate. The solvent is distilled away under reduced pressure to give 1.07 g (2.94 mmol) (Yield: 99.1%) of the compound (III-2) as crystals.

REFERENCE EXAMPLE 4

Ethyl 4-(4-fluorophenyl)-6-isopropyl-2-(N-methyl-N-methyl-sulfonylamino)pyrimidine-5-carboxylate (III-3) and Ethyl 4-(4-fluorophenyl)-6-isopropyl-2-(N-methyl-N-dimethylsulfamoylamino)pyrimidine-5-carboxylate (III-4)

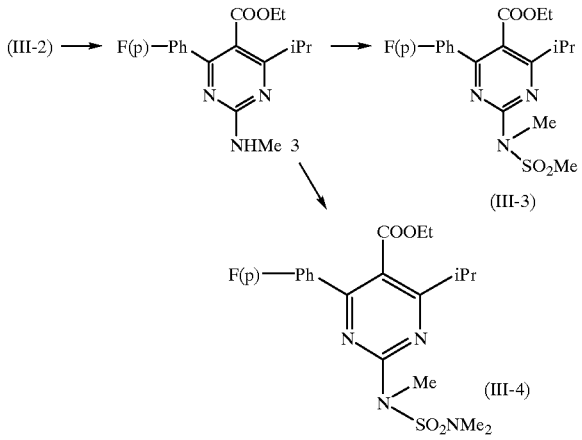

To a solution of 52.7 g (144 mmol) of the compound (III-2) in 500 ml of absolute ethanol is added gradually a solution of 71.9 ml of 5N methylamine in ethanol under ice-cooling. The reaction mixture is warmed to room temperature, stirred for 1 hour and evaporated under reduced pressure. To the residue is added water, and the mixture is extracted with ether, dried and evaporated under reduced pressure to give 46.9 g (Yield: 100%) of the compound 3. mp. 85°–86° C.

Anal Calcd. (%) for $C_{17}H_{20}N_3FO_2$: C,64.34; H,6.35; N,13.24: F,5.99. Found: C,64.42, H,6.46: N,13.30; F,6.14.

To a solution of 370 mg (1.213 mmol) of the compound 3 in 5 ml of DMF is added 60 mg of 60% NaH under ice-cooling, and the reaction mixture is stirred for 30 minutes. Methanesulfonyl chloride 208 mg is added thereto, and the mixture is warmed to room temperature and stirred for 2 hours further. To the mixture is added ice-water, and the mixture is extracted with ether. The organic layer is washed with water and dried. The solvent is evaporated under reduced pressure, and the resulting residue is washed with ether-n-pentane to give 322 mg (Yield: 57.6%) of the compound (III-3).

NMR ($CDCl_3$) δ: 1.10 (t, J=7,3H); 1.32 (d, J=7,6H); 3.24 (hept,J=7,1H); 3.52 (s,3H); 3.60 (s, 3H); 4.19 (q, J=7,2H); 7.14 (m, 2H); 7.68 (m, 2H).

To a solution of 4.13 g (13.0 mmol) of the compound 3 in 40 ml of DMF is added 0.57 g of 60% NaH under ice-cooling, and the mixture is warmed to room temperature and stirred for 1 hours. After cooling again, dimethylsulfamoyl chloride 2.43 g (16.9 mmol) is dropwise added thereto, and the mixture is stirred for 2.5 hours. To the mixture is added icewater, and the mixture is extracted with ether washed with water, dried and evaporated under reduced pressure to distill ether. The resulting residue is washed with ether-hexane to give 4.10 g (Yield: 74.2%) of the compound (III-4). mp. 114°–116° C.

Anal Calcd. (%) for $C_{19}H_{25}N_4SFO_4$: C,53.76; H,5.94; N,13.20; F,4.48. Found: C,53.74: H,5.96; N,13.19; F,4.78.

REFERENCE EXAMPLE 5

Ethyl 4-(4-fluorophenyl)-6-isopropyl-2-methoxypyrimidine-5-carboxylate (III-5) and Ethyl 4-(4-fluorophenyl)-6-isopropyl-2-(N-methyl-N-methylsulfonylhydrazino)pyrimidine-5-carboxylate (III-6)

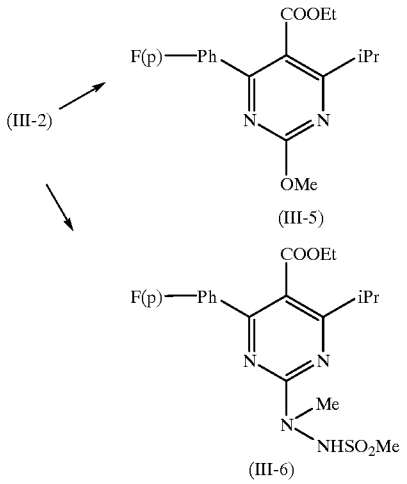

To a solution of 1.39 g (3.8 mmol) of the compound (III-2) in 60 ml of absolute methanol is added a solution of 0.41 g (7.6 mmol) of sodium methoxide under ice-cooling. The reaction mixture is warmed to room temperature gradually and stirred for 1 hour. The mixture is neutralized with acetic acid and extracted with ether. The organic layer is washed with sodium bicarbonate and water in order, dried and evaporated under reduced pressure to distill ether. The residue is subjected to column chromatography of silica gel to give 1.17 g (Yield: 96.7%) of the compound (III-5).

NMR ($CDCl_3$) δ: 1.10 (t, 3H, J=7 Hz); 1.32 (d, 6H, J=6.6 Hz); 3.21 (m, 1H); 4.08 (s, 3H); 4.18 (q, 2H, J=7 Hz); 7.07–7.74 (m, 4H).

To a solution of 2.50 g (6.77 mmol) of the compound (III-2) in 50 ml of absolute ethanol is added 0.80 g (16.93 mmol) of methyl hydrazine under ice-cooling. The reaction mixture is warmed to room temperature and stirred for 2 hours and extracted with ether. The organic layer is washed with saturated brine and dried to distill the solvent. To a mixture of 2.37 g of the thus obtained compound and a mixture of anhydrous THF and anhydrous pyridine is added 1.03 g (7.84 mmol) of methanesulfonyl chloride under testing. The reaction mixture is warmed to room temperature and stirred for 1.5 hours. To the mixture are added 3 ml of anhydrous pyridine and 1.53 g (11.65 mmol) of methanesulfonyl chloride, and the mixture is stirred for 2 hours. To the reaction mixture is added ice-water and extracted with ether. The organic layer is washed with water and the resulting oily residue is subjected to column chromatography of silica gel to give 2.75 g (Yield: 94.0%) of the compound (III6).

NMR ($CDCl_3$) δ: 1.08 (t, J=7,3H); 1.29 (d, J=7,6H); 2.96 (s, 3H); 3.24 (hept, J=7,1H); 3.59 (s, 3H); 4.16 (q, J=7,2H); 7.14 (m, 2H), 7.63 (m, 2H).

REFERENCE EXAMPLE 6

Methyl (3R)-3-(tert-butyldimethylsilyloxy)-5-oxo-6-triphenylphosphoranylidene hexanate (1) (3R)-3-(tert-butyldimethylsilyloxy)glutaric acid-1-((R)-(−)mandelic acid ester*[1] 65 g (164 mmol) is dissolved into 60 ml of methanol, a solution of sodium methoxide in methanol (28% methanol 310 ml, 1.6 mol) is added dropwise thereto under nitrogen atmosphere at 0° C. for 45 minutes at internal temperature under 7° C. The reaction mixture is stirred at 0° C. for 30 minutes and poured into a mixture of 150 ml of conc.HCl, 300 ml of water, and 500 ml of methylene chloride being stirred under ice-cooling and the organic layer is collected. The aqueous layer is extracted with 200 ml of methylene chloride, and each organic layer is washed with dil.HCl and brine in order. Each organic layer are collected and dried over anhydrous magnesium sulfate and evaporated to distill the solvent to give half ester compound.

*[1]: This compound can be prepared by the method described at page 10 in the specification of KOKAI 2-250852.

$^1$HNMR($CDCl_3$) δ: 0.08 (s, 3H); 0.09 (s, 3H); 0.86 (s, 9H); 2.52–2.73 (m, 4H); 3.08 (s, 3H); 4.55 (quint, 1H, J=6Hz).

IR ($CHCl_3$): 2880, 1734, 1712, 1438, 1305, 1096, 836 $cm^{-1}$.

[α]D=−5.0±0.4° (C=1.04, 23.5° C., $CHCl_3$).

Rf 0.32 ($CHCl_3$/MeOH=9/1).

(2) To a solution of the thus obtained half ester compound in 10 ml of ether are added dropwise triethylamine and ethyl chlorocarboxylate in order under nitrogen atmosphere at −78° C. The resulting white suspension is stirred at 0° C. for 1 hour and cooled to −78° C. The resulting precipitate is filtered under nitrogen atmosphere and the filtrate is washed with 15 ml of ether. To a suspension of 1.29 g ( 3.6 mmol) of methyl bromide triphenylphosphonium in 5 ml of THF is added dropwise butyllithium (1.6M hexane, 2.25 ml, 3.6 mmol) under nitrogen atmosphere at −78° C. The reaction mixture is stirred at 0° C. for 1 hour and cooled to −78° C. and added dropwise to the solution of thus obtained active ester compound in ether. The reaction mixture is washed with 5 ml of THF and stirred at 0° C. for 1 hour, and 10 ml of 5% sodium hydrogencarbonate is added thereto. The reaction mixture is stirred for 5 minutes and extracted with ethyl acetate and the organic layer is separated and the remaining aqueous layer is extracted with ethyl acetate. Each organic layer is collected and washed with brine, dried over anhydrous magnesium sulfate and concentrated. The obtained residue is subjected to column chromatography of silica gel eluting with ether-ethyl acetate and crystallized from ether-hexane to give objective compound.

$^1$HNMR ($CDCl_3$)δ: 0.04 (s, 3H); 0.06 (s, 3H); 0.83 (s, 9H); 2.4–2.9 (m, 4H); 3.64 (s, 3H); 3.74 (d, 1H); 4.5–4.7 (m, 1H); 7.4–7.8 (m, 15H).

IR ($CHCl_3$): 2380, 1730, 1528, 1437, 1250, 1106, 835 $cm^{-1}$.

[α]D=−6.2° (C=1.27, 22.0° C., $CHCl_3$).

mp.:77.5°–78.5° C., Rf=0.48 ($CHCl_3$/MeOH=9/1).

Anal Calcd. (%) for $C_{31}H_{39}O_4PS$: C, 69.63; H,7.35; P,5.79. Found: C, 69.35; H,7.35; P,6.09.

EXAMPLE 1

Sodium (+)-7-[4-(4-fluorophenyl)-6-isopropyl-2-(N-methyl-N-methylsulfonylaminopyrimidin)-5-yl]-(3R,5S)-dihydroxy-(E)-6-heptenate (I a-1)

(1) To a solution of 322 mg of the compound (III-3) obtained in Reference Example 2 in 7 ml of anhydrous toluene is added dropwise 1.4 ml of DIBAL-H in 1.5M toluene at −74° C., and the reaction mixture is stirred for 1 hour and acetic acid is added thereto. The mixture is extracted with ether, and the organic layer is washed with sodium bicarbonate and water, dried and evaporated under reduced pressure to distil ether. The obtained residue is subjected to column chromatography of silica gel eluting with methylene chloride/ether (20/1) to give 277 mg (Yield: 96.1%) of [4-(4-fluorophenyl)-6-isopropyl-2-(N-methyl-N-methylsulfonylamino)pyrimidin-5-yl]methanol 4.

4

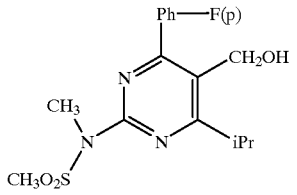

(2) A suspension of 277 mg of the thus obtained compound 4, 190 mg of 4-methylmorpholin-N-oxide, 6 mg of TPAP, 1.0 g of powder molecular sieve 4A, and 10 ml of methylene chloride is stirred for 2 hours. The insoluble matter is filtered off and the two-thirds of the filtrate is distilled away under reduced pressure. The resulting residue is subjected to column chromatography of silica gel eluting with methylene chloride to give 196 mg (Yield: 71.2%) of 4-(4-fluorophenyl)-6-isopropyl-2-(N-methyl-N-methylsulfonylamino)-5-pyrimidinecarbardehyde as crystals.

5

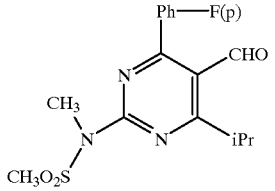

(3) A solution of 190 mg of the compound 5, 450 mg of methyl (3R)-3-(tert-butyldimethylsilyloxy)-5-oxo-6-triphenylphosphoranylidene hexanate (Reference Example 6), and 5 ml of acetonitrile is refluxed under heating for 14 hours and evaporated under reduced pressure to distill acetonitrile. The resulting residue is subjected to column chromatography of silica gel eluting with methylene chloride to give 233 mg (Yield: 71.3%) of methyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenate 6 as syrup.

6

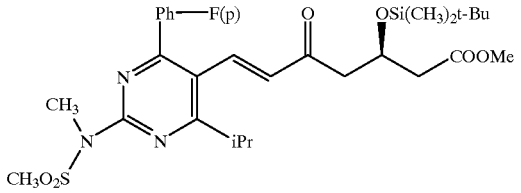

(4) To a solution of 16 g of the compound 6 in 100 ml of acetonitrile is added dropwise a solution of 48% hydrogen flouride in 400 ml of acetonitrile (1:19) under ice-cooling, and the mixture is warmed to room temperature and stirred for 1.5 hours. The reaction mixture is neutralized with sodium bicarbonate and extracted with ether. The organic layer is washed with sodium chloride, dried and evaporated under reduced pressure to distil ether to give 13 g (Yield: 100%) of methyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenate 7 as syrup.

7

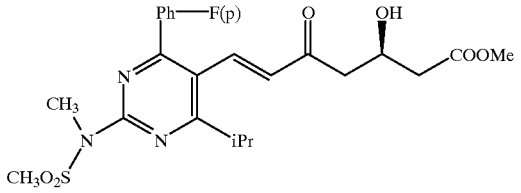

(5) To a solution of 13 g of the compound 7 in 350 ml of anhydrous THF and 90 ml of methanol is added a solution of 29.7 ml of 1M diethylmethoxyborane-THF at −78° C., and the mixture is stirred at the same temperature for 30 minutes. To the mixture is added 1.3 g of $NaBH_4$, and the mixture is stirred for 3 hours. Acetic acid 16 ml is added thereto, and the mixture is adjusted to pH 8 with saturated sodium bicarbonate and extracted with ether. The organic layer is washed with water, dried and evaporated ether under reduced pressure. To the resulting residue is added methanol and the mixture is evaporated under reduced pressure for three times. The resulting residue is subjected to column chromatography of silica gel eluting with methylene chloride/ether (3/1) to give 11.4 g (Yield: 85.2%) of methyl 7-[4-(4-fluorophenyl)-6-iso-propyl-2-methyl-N-methylsulfonylamino)pyrimidin-5-yl]-(3R,5S)-dihydroxy-(E)-6-heptenate as syrup.

(Ib-1)

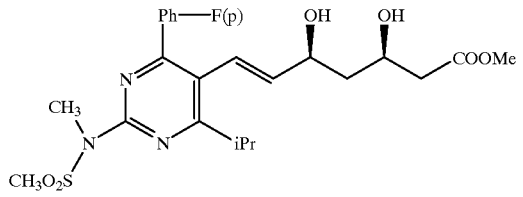

NMR ($CDCl_3$) δ: 1.27 (d, J=7,6H); 1.53 (m, 2H); 2.47 (d, J=6,2H); 3.36 (hept, J=2H); 3.52 (s, 3H); 3.57 (s, 3H); 3.73 (s, 3H); 4.20 (m, 1H); 4.43 (m, 1H); 5.45 (dd, J=5,16, 1H); 6.64 (dd, J=2,16, 1H); 7.09 (m, 2H); 7.64 (m, 2H).

(6) To a solution of 11.4 g of the compound (I b-1) in 160 ml of ethanol is added 223 ml of 0.1N sodium hydroxide under ice-cooling. The reaction mixture is warmed to room temperature and stirred for 1 hour. The solvent is distilled away under reduced pressure, and ether is added to the resulting residue and the mixture is stirred to give 11.0 g (Yield: 95.0%) of the objective compound (I a-1) as powdery crystals.

(Ia-1)

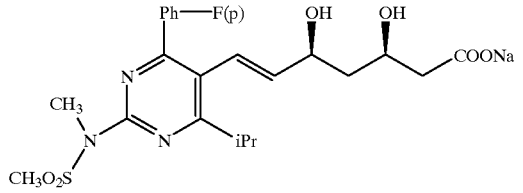

$[\alpha]_D$=+18.9±0.6° (C=1.012, 25.0° C., $H_2O$).

NMR ($CDCl_3$) δ: 1.24 (d, J=7,6H); 1.48 (m, 1H); 1.65 (m, 1H); 2.27 (dd,J=2,6.2H); 3.41 (hept, J=7,1H); 3.48 (s, 3H); 3.59 (s, 3H); 3.73 (m, 1H); 4.32 (m 1H); 5.49 (dd, J=7,16 1H); 6.62 (d, J=16,1H); 7.19 (m, 2H); 7.56 (m, 2H).

EXAMPLE 2

Sodium (+)-7-[4-(4-fluorophenyl)-6-isopropyl-2-(N-acetyl-N-methylamino)pyrimidin-5-yl]-(3R,5S)-dihydroxy-(E)-6-heptenate (I a-2)

(1) Ethyl 4-(4-fluorophenyl-6-isopropyl-2-methylaminopyrimidine-5-carboxylate 3 838 mg obtained in Reference Example 4 is allowed to react in the same manner as in Example 1 (1) and (2) to give 157 mg of 4-(4-fluorophenyl)-6-isopropyl-2-methylaminopyrimidine-5-carbaldehyde.

(2) A solution of 157 mg of thus obtained aldehyde compound in 4 ml of anhydrous DMF is reacted with 25 mg of 60% NaH under ice-cooling for 30 minutes, 0.05 ml of acetylchloride is added thereto and the mixture is stirred for 1 hour. The mixture is added with ice and extracted with ether. The organic layer is washed with water and dried and concentrated to distill the solvent to give 167 mg (Yield: 93.4%) of 4-(4-fluorophenyl)-6-isopropyl-2-(N-acetyl-N-methylamino)pyrimidine-5-carbardehyde. Thus obtained aldehyde compound is reacted in the same manner as in Example 1 (3)–(5) to give methyl 7-[4-(4-fluorophenyl)-6-isopropyl-2-(N-acetyl-N-methylaminopyrimidin)-5-yl]-(3R,5S)-dihydroxy-(E)-6-heptenate (I b-2).

NMR ($CDCl_3$)δ: 1.27 (d, J=7,6H); 1.54 (m, 2H); 2.48 (d, J=6,2H); 2.52 (s, 3H); 3.39 (hept, J=7, 1H); 3.60 (s, 3H); 3.58 (brs, 1H); 3.74 (s, 3H): 4.21 (m, 1H); 4.48 (m, 1H); 5.50 (dd, J=5,16, 1H); 6.66 (dd, J=2,16); 7.11 (m, 2H); 7.61 (m, 2H).

(3) The thus obtained compound (I b-2) is reacted in the same manner as Example 1 (6) to give the objective compound (I a-2).

(Ia-2)

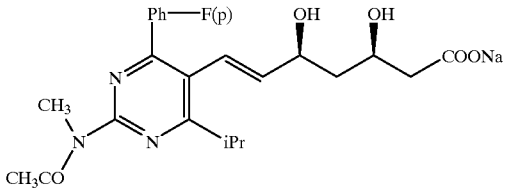

NMR ($CDCl_3$)δ: 1.27 (d, J=7,6H); 1.57 (m, 2H): 2.17 (s, 3H); 2.27 (d, J=6,2H); 3.72 (s, 3H); 3.50 (hept, J=7, 1H); 3.70 (m, 1H); 4.35 (q, J=6,1H); 5.59 (dd, J=5,16, 1H); 6.54 (d, J=16, 1H); 7.24 (m, 2H): 7.59 (m, 2H).

EXAMPLE 3–6

As a starting material, each pyrimidine carboxylate (III) obtained in Reference Example 1–3 is reacted in the same manner as Example 1 or 2 to give the compound (I b) and (I a). Their physical constants are shown in Table 1–3.

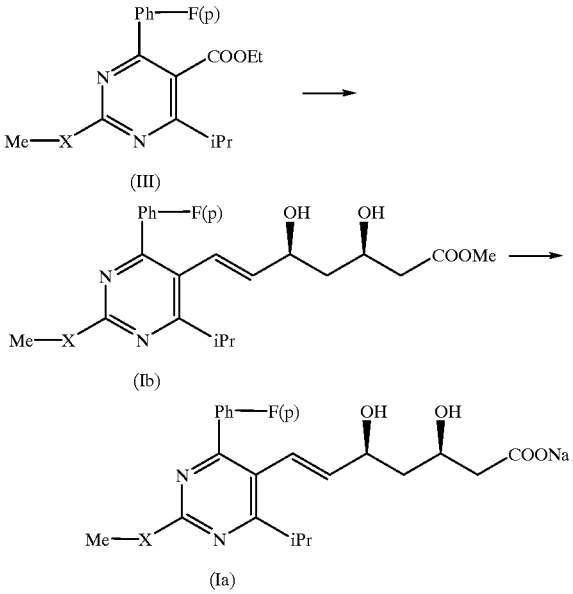

TABLE 1

| Ex. No. | Startup material | Product NMR δ |
|---|---|---|
| 3 | (Ill-1) | 1b-3(X: S)Yield 96.0% ($CDCl_3$, 1.26(d, J = 7.6H): 1.52(m, 2H): 2.47(d, J = 6, 2H): 2.60(s, 3H): 3.33(hept, J = 7, 1H): 3.73 (s, 3H): 4.18(m, 1H): 4.44(m, 1H): 5.44(dd, J = 5, 16, 1H): 6.60(dd, J = 2, 16, 1H), 7.07(m, 2H): 7.58(m, 2H)<br>1a-3(X: S)Yield 87.3% ($D_2O$) 1.20(d, J = 7, 6H): 1.47(m, 1H): 1.61(m, 1H): 2.26(m, 2H), 2.54(s, 3H): 3.36(hept, J = 7, 1H): |

TABLE 1-continued

| | | |
|---|---|---|
| | | 3.71(m, 1H): 4.29(m, 1H): 5.43(dd, J = 6, 16, 1H): 6.55(d, J = 16, 1H): 7.16(m, 2H), 7.47 (m, 2H) |
| 4 | (Ill-2) | 1b-4(X: $SO_2$): Yield 93.7% ($CDCl_3$) 1.31(d, J = 7, 6H): 1.52(m, 2H): 2.48(d, J = 6, 2H): 3.40(s, 3H); 3.47(hept, J = 7, 1H); 3.74 (s, 3H): 3.87(brs, 1H): 4.23(m, 1H): 4.49 (m, 1H); 5.59(dd, J = 5, 16H, 1H); 6.74(d, d, J = 2, 16, 1H); 7.12(m, 2H): 7.69(m, 2H) 1a-4(X: $SO_2$): Yield 70.9% ($D_2O$) 1.27(d, d, J = 7, 2, 6H); 1.60(m, 2H); 2.25(J = 6, d, 2H): 3.44(s, 3H): 3.51(hept, J = 7, 1H): 3.70(m, 1H): 4.33(q, J = 6, 1H): 5.65(d, d, J = 5, 16, 1H): 6.71(d, J = 16, 1H): 7.23(m, 2H); 7.60 7.60(m, 2H) |

TABLE 2

| Ex. No. | Starting material | Product NMR δ |
|---|---|---|
| 5 | (Ill-5) | 1b-5(X: O): ($CDCl_3$) 1.27(d, 6H, J = 6.6 Hz): 1.35–1.68(m, 2H): 2.47 (m, 2H): 3.34(m, 1H): 3.78(s, 3H): 4.03(s, 3H): 4.19(m, 1H); 4.43(m, 1H): 5.43(dd, 1H, J = 5.6, 16 Hz): 6.59(dd, 1H, J = 1.4, 16 Hz): 7.03–7.64(m, 4H) 1a-5(X: O) Yield 57.7% ($CDCl_3$, $CD_3OD$) 1.27(d, 6H, J = 6.6 Hz): 1.35–1.68(m, 2H): 2.17–2.43(m, 2H): 3.36(m, 2H), 4.05(s, 3H): 4.37 (m, 2H): 5.48(dd, 1H, J = 5.6, 16 Hz): 6.54(dd, 1H, J = 1.4, 16 Hz): 7.06–7.65(m, 4H) |
| 6 | (Ill-4) | 1b-6(X: N—$SO_2NMe_2$): ($CDCl_3$) 1.26(d, 6H, J = 6.6 Hz); 1.38–1.62(m, 2H): 2.47 (d, 2H, J = 5.8); 2.84(s, 6H), 3.35(m, 1H): 3.64(s, 3H); 3.74(s, 3H); 4.20(m, 1H): 4.44 (m, 1H); 5.42(dd, 1H, J = 5.4, 16 Hz): 6.60 (dd, 1H, J = 1.2, 16 Hz): 7.03–7.64(m, 4H) 1a-6: Yield: 91.2% ($CDCl_3$, $CD_3OD$) 1.26(d, 6H, J = 6.6 Hz); 1.36–1.69(m, 2H): 2.15–2.50(m, 2H); 2.85 (s, 6H); 3.41(m, 2H): 3.64 (s, 3H): 4.04(m, 1H): 4.37(m, 1H); 5.48 (dd, 1H, J-5.6, 16 Hz): 6.54(dd, 1H, J-1, 16 Hz): 7.05–7.66(m, 4H) |

TABLE 3

| Ex. No. | Starting material | Product NMR δ |
|---|---|---|
| 7 | (Ill-6) | 1b-7(X: N—$NHSO_2Me$): Yield: 87.8% ($CDCl_3$) 1.24(d, J = 7, 6H): 1.51(m, 2H): 2.47(d, J = 6, 2H); 2.95(s, 3H); 3.35(hept, J = 7, 1H); 3.46 (d, J = 2, 1H): 3.55(s, 3H); 3.66(d, J = 2, 1H): 3.74 (s, 3H): 4.18(m, 1H): 4.44(m, 1H): 5.41 (dd, J = 5, 16, 1H); 6.58(dd, J = 2, 16, 1H); 7.09(m, 2H); 7.58(m, 2H), 7.70(s, 1H) 1a-7(X: N—$NHSO_2Me$): Yield: 74.7% ($D_2O$) 1.23(d, J = 7, 6H): 1.51(m, 2H): 2.26(d, J = 6, 2H) 3.10(s, 3H); 3.37(hept, J = 7, 1H): 3.44 (s, 3H): 3.70(m, 1H). 4.29(q, J = 6, 1H): 5.39 (dd, J = 5, 16, 1H): 6.58(d, J = 16, 1H): 7.19(m, 2H):7.52(m, 2H) |

EXAMPLE 7

Calcium salt of the compound (I a-1) (sodium salt) 1.50 g (3.00 mmol) is dissolved in 15 ml of water and stirred at room temperature under nitrogen atmosphere, successively 3.00 ml (3.00 mmol) of 1 mol/L calcium chloride 3.00 ml (3.00 mmol) is added dropwise thereto over 3 minutes. The reaction mixture is stirred at the same temperature for 2 hours, and the resulting precipitate is collected, washed with water and dried to give 1.32 g of calcium salt as powdery. This compound started to melt at a temperature of 155° C., but the definitive melting point is ambiguous.

$[\alpha]D=+6.3° \pm 0.2°$ (C=2.011, 25.0° C., MeOH).

Anal Calcd. (%) for $C_{22}H_{27}N_3O_6SF$ . 0.5Ca . 0.5$H_2O$: C,51.85; H,5.53; N,8.25; F,3.73; Ca,3.93. Found: C,51.65; H,5.51; N,8.47; F,3.74; Ca,4.07.

Biological Activity

Experiment

The HMG-CoA reductase inhibitory effect (1) Preparation of rat liver microsome Sprague-Dawley rats, which were in free access to ordinary dietes containing 2% cholestyramine and water for 2 weeks, were used for the preparation of rat liver microsome. The thus obtained microsome was the purified according to the manner by Juroda et al., Biochem. Biophys. Act, 486, 70 (1977). The microsomal fraction obtained by centrifugation at 105,000×g was washed once with a buffered solution containing 15 mM nicotinamide and 2 mM magnesium chloride (in a 100 mM potassium phosphate buffer, pH 7.4). It was homogenized with a buffer containing nicotinamide and magnesium chloride at the same weight as the liver employed. The thus obtained homogenate was cooled down and kept at −80° C.

(2) Measurement of the HMG-CoA reductase inhibitory activities

The rat liver microsome sample (100 μl), which was preserved at −80° C., was fused at 0° C. and diluted with 0.7 ml of a cold potassium phosphate buffer (100 mM, pH7.4). This was mixed with 0.8 ml of 50 mM EDTA (buffered with the aforementioned potassium phosphate buffer) and 0.4 ml of 100 mM dithiothreitol solution (buffered with the aforementioned potassium phosphate buffer), and the mixture was kept at 0° C. The microsome solution (1.675 ml) was mixed with 670 μl of 25 mM NADPH (buffered with the aformentioned potassium phosphate buffer), and the solution was added to the solution of 0.5 mM $[3^{-14}]$(HMG-CoA (3mCi/mmol). A solution (5 μl) of sodium salt of the test compound dissolved in potassium phosphate buffer is added to 45 μl of the mixture. The resulting mixture was incubated at 37° C. for 30 minutes and cooled. After termination of the reaction by addition of 10 μl of 2N·HCl, the mixture was incubated again at 37° C. for 15 minutes and then 30 μl of this mixture was applied to thin-layer chromatography of silica gel of 0.5 mm in thickness (Merck AG, Art 5744). The chromatograms were developed in toluene/acetone (1/1) and the spot, whose Rf value was between 0.45 to 0.60, were scraped. The obtained products were put into a vial containing 10 ml of scintillator to measure specific radio-activity with scintillation counter. The activities of the present compounds are shown in Table 4 as comparative ones based on the assumption that the activity of Mevinolin (sodium salt) as reference drug is 100.

TABLE 4

| Test Compound | HMG-CoA reductase inhibitory activities |
|---|---|
| 1a-1 | 442 |
| 1a-3 | 385 |
| 1a-5 | 279 |

TABLE 4-continued

| Test Compound | HMG-CoA reductase inhibitory activities |
|---|---|
| 1a-7 | 260 |
| Mevinolin Na | 100 |

From the test data, the compounds of the present invention exhibit HMG-CoA reductase inhibition activities superior to Mevinolin.

What is claimed is:

[1. A compound represented by the formula (I):

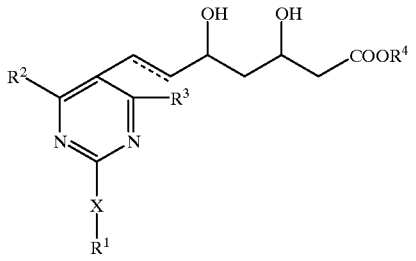

wherein $R^1$ is (1) lower alkyl which may have 1 to 3 substitutents independently selected from the group consisting of halogen, amino, and cyano, (2) $C_6$ to $C_{12}$ aromatic group which may have 1 to 3 substituents independently selected from the group consisting of lower alkyl, halogen, amino, and cyano, or (3) $C_1$ to $C_6$ lower alkyl substituted by $C_6$ to $C_{12}$ aromatic group which may have 1 to 3 substituents independently sel-ected from the group consisting of lower alkyl, halo-gen, amino, and cyano; $R^2$ and $R^3$ each is independently (1) hydrogen, (2) lower alkyl which may have 1 to 3 substituents independently selected from the group consisting of halogen, amino, and cyano, or (3) $C_6$ to $C_{12}$ aromatic group which may have 1 to 3 substituents independently selected from the group consisting of lower alkyl, halogen, amino, and cyano; $R^4$ is (1) hydro-gen, (2) lower alkyl, or a cation capable of forming a non-toxic pharmaceutically acceptable salt; X is sulfur, oxygen, or sulfonyl, or imino which may be substituted by formyl, acetyl, propionyl, butyryl, isobutyryl, vale-ryl, isovaleryl, amino substituted by sulfonyl or alkyl-sulfonyl, and sulfonyl substituted by alkyl, amino or alkylamino, the dotted line represents the presence or absence of a double bond, or the corresponding ring-closed lactone.]

[2. The compound claimed in claim 1, wherein X is imino which may be substituted by formyl, acetyl, pro-pionyl, butyryl, isobutyryl, valeryl, isovaleryl, amino substituted by sulfonyl or alkylsulfonyl, or sulfonyl substituted by alkyl, amino or alkylamino.]

[3. The compound claimed in claim 2, wherein X is imino which may be substituted by formyl, acetyl, pro-pionyl, butyryl, isobutyryl, valeryl, isovaleryl, alkylsul-fonylamino, or alkylsulfonyl.]

[4. The compound claimed in claim 1 having the (3R, 5S)-dihydroxy configuration.]

[5. A pharmaceutical composition comprising an ef-fective amount of the compound claimed in claim 1 as an active ingredient, in combination with a pharmaceu-tical excipient.]

*6. The compound 7-(4-(4-fluorophenyl)-6-isopropyl-2-(N-methyl-N-methylsulfonylamino)pyrimidin-5-yl)-(3R,5S)-dihydroxy-(E)-6-heptenoic acid in the form of a non-toxic pharmaceutically acceptable salt thereof.*

*7. The compound of claim 6 in the form of a sodium salt.*

*8. The compound of claim 6 in the form of a calcium salt.*

* * * * *